US00PP28949P3

(12) United States Plant Patent
Ikeno et al.

(10) Patent No.: US PP28,949 P3
(45) Date of Patent: Feb. 6, 2018

(54) COLEUS PLANT NAMED 'SAKCOL019'

(50) Latin Name: ***Solenostemon* sp.**
Varietal Denomination: SAKCOL019

(71) Applicant: Sakata Seed Corporation, Yokohama (JP)

(72) Inventors: Masanori Ikeno, Kakegawa (JP); Rei Takahashi, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,095

(22) Filed: Mar. 30, 2016

(65) Prior Publication Data

US 2017/0290247 P1 Oct. 5, 2017

(51) Int. Cl.
*A01H 5/12* (2006.01)

(52) U.S. Cl.
USPC ..... Plt./373
CPC ..... *A01H 5/12* (2013.01)

(58) Field of Classification Search
USPC ..... Plt./373
See application file for complete search history.

*Primary Examiner* — Keith O Robinson
(74) *Attorney, Agent, or Firm* — Bethany R. Roahrig; Barbara Campbell; Cochran Freund & Young LLC

(57) ABSTRACT

A coleus plant particularly distinguished by large leaves and yellow-green leaves with green margins, is disclosed.

2 Drawing Sheets

Genus and species: *Solenostemon* sp.
Variety denomination: 'SAKCOL019'.

BACKGROUND OF THE NEW PLANT

The present invention comprises a new and distinct variety of coleus, botanically known as *Solenostemon* sp., and hereinafter referred to by the variety name 'SAKCOL019'.

'SAKCOL019' originated from a cross-pollination conducted in October 2012 in Kakegawa, Japan among multiple plants of six unpatented proprietary coleus lines designated '0-8C-3A-1B-5B-11D-3', '12TH-2', '12C-3', '12M-4', '12H-5' and '12TL-1'. The cross-pollination was conducted in a cage using bees. 2,600 seeds were harvested from the '12C-3' plants. The seeds harvested from the '12C-3' plants are composed of hybrid seeds and self-pollinated seeds.

The seeds obtained from the '12C-3' plants were sown and a single plant selection designated 'L2013-CO040' was selected for its multi-colored leaf pattern displaying a yellow-green leaf and rose colored veins, creeping plant habit and small leaves. The breeder confirmed that 'L2013-CO040' was fixed and stable. 'L2013-CO040' was subsequently named 'SAKCOL019'.

The new plant was first asexually propagated in 2013 in Japan and has been asexually reproduced by vegetative cuttings for almost three years in Japan. The present invention has been found to retain its distinctive characteristics through successive asexual propagations by vegetative cuttings.

'SAKCOL019' has not been made publicly available or sold more than one year prior to the filing date of this application.

SUMMARY OF THE NEW PLANT

The following are the most outstanding and distinguishing characteristics of the new variety when grown under normal horticultural practices in Salinas, Calif.

1. Large leaves; and
2. Yellow-green leaves with green margins.

DESCRIPTION OF THE PHOTOGRAPHS

This new coleus plant is illustrated by the accompanying photographs which show the overall plant habit, and foliage of a plant aged 7 months old. The colors are as true as can be reasonably obtained by conventional photographic procedures.

Figure 1:
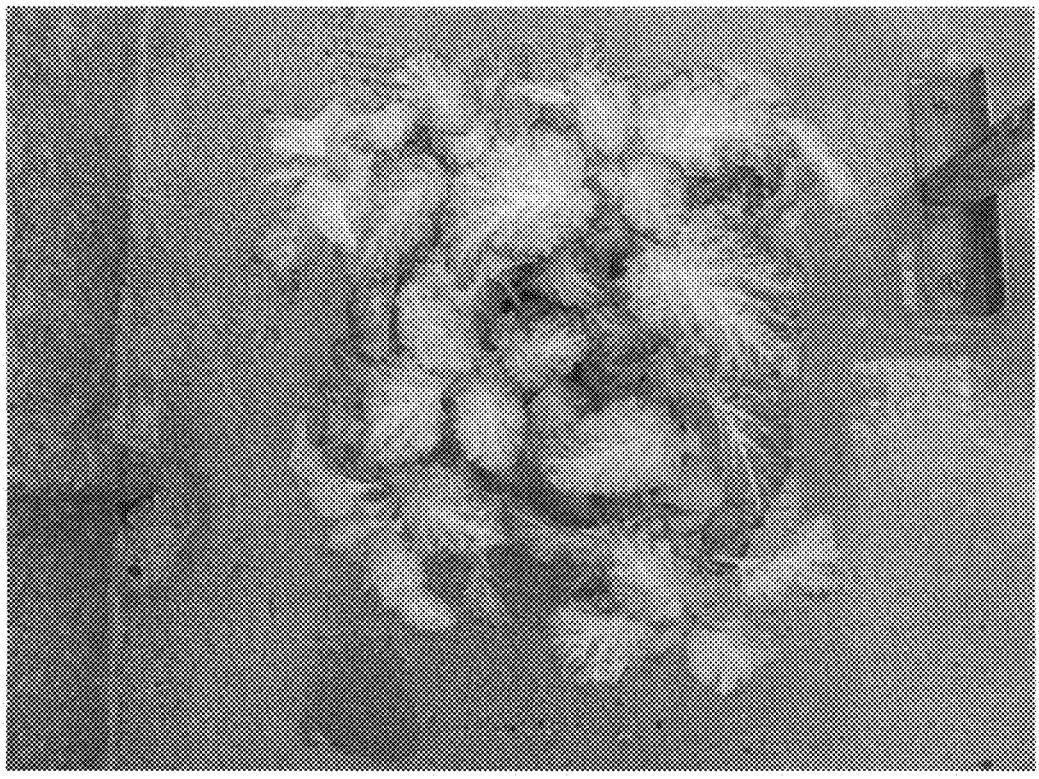
Figure 2:
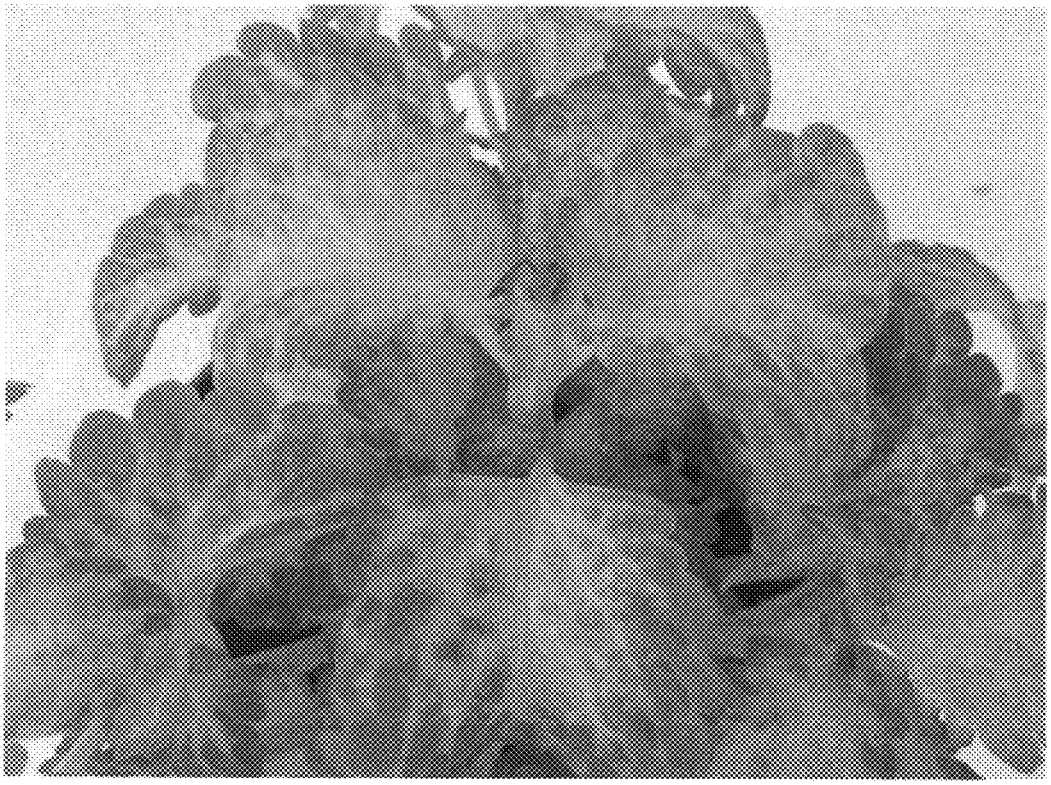

FIG. 1 shows the whole plant, including habit and foliage.
FIG. 2 shows a close-up of the foliage.

DESCRIPTION OF THE NEW VARIETY

The following detailed descriptions set forth the distinctive characteristics of 'SAKCOL019'. The data which defines these characteristics were collected from plants grown 7 months from transplant into 4-inch pots from rooted cuttings in Salinas, Calif., under greenhouse conditions. Color references are to The Royal Horticultural Society Colour Chart, $4^{th}$ edition. Anatomic labels are from *The Cambridge Illustrated Glossary of Botanical Terms*, by M. Hickey and C. King, Cambridge University Press.

Classification:
*Family*.—Lamiaceae.
*Botanical name*.—*Solenostemon* sp.
*Common name*.—Coleus.
*Denomination*.—'SAKCOL019'.

Plant:
*Type*.—Annual.
*Habit*.—Compact, semi-trailing.
*Form*.—Compact and dense, 5 main branches.
*Height*.—22.0 cm.
*Spread*.—35.0 cm.
*Propagation type*.—Vegetative cuttings.

Environmental conditions for plant growth: The terminal 1.0 to 1.5 inches of an actively growing stem was excised.

The vegetative cuttings were propagated for five to six weeks. The base of the cuttings were dipped for 1 to 2 seconds in a 1:9 solution of DIP 'N GROW (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24 degrees C.

Lateral branches:

*Length.*—16.5 cm.
*Diameter.*—7.0 mm to 8.0 mm.
*Internode length.*—3.0 cm to 4.5 cm.
*Strength.*—Branches separate easily.
*Aspect.*—Large.
*Shape in cross-section.*—Square.
*Texture.*—Very slight pubescent.
*Pubescence color.*—RHS N155A (White).
*Flowering branch.*—Present.

Leaves:

*Arrangement.*—Opposite.
*Length.*—9.0 cm.
*Width.*—6.2 cm.
*Broadest part of the leaf blade.*—Middle.
*Shape.*—Cordate.
*Apex.*—Lanceolate.
*Base.*—Cordate.
*Margin.*—Crenate.
*Texture, upper surface.*—Very slight pubescence, with blistering.
*Texture, lower surface.*—Blistered with pronounced venation, glabrous.
*Venation pattern.*—Reticulate.
*Vein color, upper surface.*—Closest to RHS 1D (Yellow-Green).
*Vein color, lower surface.*—Closest to RHS 1D (Yellow-Green).
*Petiole length.*—2.7 cm.
*Petiole diameter.*—3.0 mm.
*Petiole color.*—RHS 154C (Yellow-Green).
*Petiole texture.*—Very slight pubescent.
*Variegation.*—Present.
*Leaf color.*—Multicolored, yellow towards center with green towards leaf margin. Upper surface: Closest to but darker than RHS 1B (Yellow) with blotches of RHS 137A (Green) increasing towards margin. Lower surface: Closest to RHS 12C (Yellow) with increasing blotches of RHS 137C (Green) towards margin.

Flowers: Terminal flower bud observed having multiple buds and forming an elongated pyramid shape.

*Bud length.*—1.8 cm.
*Bud diameter.*—5.0 mm
*Bud color.*—RHS 145A (Yellow-Green).
*Stalk length.*—8.6 cm.
*Stalk diameter.*—3.0 mm.
*Stalk color.*—Closest to RHS 160A (Greyed-Yellow).
*Flower color.*—RHS 92A (Violet-Blue) with RHS 155C (White) at base.

Temperature tolerance: 2 degrees C. to 35 degrees C.

Disease or insect resistance: No disease or insect resistance observed.

COMPARISON WITH PARENTAL LINES AND KNOWN VARIETY

'SAKCOL019' is a new and distinct cultivar of coleus owning to its unique multicolored leaf pattern and compact and dense semi-creeping habit. It is distinguished from its parents as described in Table 1 below.

TABLE 1

Comparison with Parental Lines

| Parental lines | Leaf color, upper surface | Plant habit |
|---|---|---|
| '0-8C-3A-1B-5B-11D-3' | Inner leaf: rose color; Outer leaf: dark brown with green edge and large leaves. | Erect |
| '12TH-2' | Inner leaf: dark brown; Outer leaf: green with small leaves. | Creeping |
| '12C-3' (female parent) | Leaf color is yellow-green with rose colored veins with small leaves. | Creeping |
| '12M-4' | Inner leaf: dark brown; Outer leaf: red with light green edge with wavy leaves | Erect |
| '12H-5' | Leaf color are shades red with a dark green edge and large leaves. | Erect |
| '12TL-1' | Inner leaf: dark brown; Outer leaf: rose with small leaves. | Creeping |
| **Subject variety** | **Leaf color** | **Plant habit** |
| 'SAKCOL019' | Closest to but darker than RHS 1B (Yellow) with blotches of 137A (Green) increasing towards margin. | Semi-creeping |

'SAKCOL019' is most similar to the commercial variety COLORBLAZE 'Lime Time', also known as 'UF12-30-6' (U.S. Plant Pat. No. 27,140); however, there are differences as listed in Table 2 below.

TABLE 2

Comparison with Similar Variety

| Characteristic | 'SAKCOL019' | COLORBLAZE 'Lime Time' |
|---|---|---|
| Leaf color, upper surface | Closest to but darker than RHS 1B (Yellow) with blotches of RHS 137A increasing towards margin. | RHS N144A |
| Leaf color, lower surface | Closest to RHS 12C (Yellow) with increasing blotches of RHS 137C towards margin. | RHS 145A |
| Plant growth habit | Compact, Semi-creeping | Upright |

We claim:

1. A new and distinct variety of coleus plant named 'SAKCOL019' as illustrated and described herein.

* * * * *